United States Patent
Storz et al.

(10) Patent No.: US 9,526,481 B2
(45) Date of Patent: Dec. 27, 2016

(54) POWER UNIT, MEDICAL HANDHELD DEVICE AND ARRANGEMENT

(75) Inventors: Olaf Storz, Tuttlingen (DE); Andreas Schmal, Emmingen-Liptingen (DE)

(73) Assignee: Olaf Storz, Tuttlingen (DE)

( * ) Notice: Subject to any disclaimer, the term of this patent is extended or adjusted under 35 U.S.C. 154(b) by 889 days.

(21) Appl. No.: 13/613,264

(22) Filed: Sep. 13, 2012

(65) Prior Publication Data

US 2013/0240231 A1    Sep. 19, 2013

Related U.S. Application Data

(60) Provisional application No. 61/537,587, filed on Sep. 22, 2011.

(30) Foreign Application Priority Data

Sep. 14, 2011   (DE) .................. 10 2011 113 126
Aug. 1, 2012    (DE) .................. 10 2012 015 091

(51) Int. Cl.
  *B25C 5/00*  (2006.01)
  *A61B 17/14* (2006.01)
  *A61B 17/00* (2006.01)
  *A61B 17/16* (2006.01)

(52) U.S. Cl.
  CPC ........... *A61B 17/00* (2013.01); *A61B 17/1622* (2013.01); *A61B 17/14* (2013.01); *A61B 17/1626* (2013.01); *A61B 17/1628* (2013.01); *A61B 2017/00398* (2013.01); *A61B 2017/00482* (2013.01); *A61B 2017/00734* (2013.01)

(58) Field of Classification Search
  CPC .......... H02P 5/00; B23Q 17/00; B23Q 17/50; A61B 17/072
  USPC ................ 173/216, 217; 318/3; 606/80, 180
  See application file for complete search history.

(56) References Cited

U.S. PATENT DOCUMENTS

| | | | | |
|---|---|---|---|---|
| 4,091,880 A | * | 5/1978 | Troutner et al. ............... | 173/217 |
| 6,860,792 B2 | * | 3/2005 | Krondorfer ........... | B24B 23/022 |
| | | | | 451/344 |
| 2005/0218867 A1 | * | 10/2005 | Phillips ..................... | B25F 5/02 |
| | | | | 320/114 |
| 2006/0217729 A1 | * | 9/2006 | Eskridge et al. ............... | 606/80 |
| 2006/0234617 A1 | * | 10/2006 | Francis ................ | B23D 59/001 |
| | | | | 452/174 |

(Continued)

FOREIGN PATENT DOCUMENTS

DE    3317398    11/1984

*Primary Examiner* — Nathaniel Chukwurah
(74) *Attorney, Agent, or Firm* — Von Rohrscheidt Patents

(57) ABSTRACT

The invention relates to a power unit which is receivable in or at a medical handheld medical device in a disengageable manner, wherein the power unit includes at least a voltage source, a motor and/or a circuit board, wherein the power unit includes an arrangement for identifying which is configured to identify at least one feature of the medical handheld device and to emit a signal caused by the identified feature or based on the identified feature. The invention furthermore relates to a medical handheld device, comprising at least one power unit according to one of the preceding claims and/or at least one feature which is provided to be identified through the identification arrangement. The invention furthermore relates to an arrangement for identifying a medical handheld device that is connected with the power unit according to the invention.

23 Claims, 7 Drawing Sheets

(56) References Cited

U.S. PATENT DOCUMENTS

| | | | |
|---|---|---|---|
| 2007/0213692 A1* | 9/2007 | Neubauer | A61B 17/14 606/1 |
| 2007/0270784 A1* | 11/2007 | Smith et al. | 606/1 |
| 2008/0077149 A1* | 3/2008 | Hoegerle | A61B 17/1613 606/80 |
| 2008/0170841 A1* | 7/2008 | Schneider et al. | 388/800 |
| 2008/0255418 A1* | 10/2008 | Zemlok et al. | 600/118 |
| 2009/0229842 A1* | 9/2009 | Gray | H01M 2/1055 173/20 |
| 2011/0155785 A1* | 6/2011 | Laurent et al. | 227/180.1 |
| 2011/0198103 A1* | 8/2011 | Suzuki | B25F 5/00 173/46 |
| 2011/0284257 A1* | 11/2011 | Ogino | B25F 5/00 173/217 |
| 2011/0290241 A1* | 12/2011 | Maeda | A61M 11/005 128/200.14 |
| 2012/0071796 A1* | 3/2012 | Smith | A61B 17/32009 601/3 |

* cited by examiner

POWER UNIT, MEDICAL HANDHELD DEVICE AND ARRANGEMENT

RELATED APPLICATIONS

This application claims priority from and incorporates by reference German Patent Application DE 10 2011 113 126.8, filed on Sep. 14, 2011, German Patent Application De 10 2012 015 091.1, filed on Aug. 8, 2012 and U.S. Provisional Patent Application 61/537,587 filed on Sep. 22, 2011.

FIELD OF THE INVENTION

The present invention relates to a power unit. It furthermore relates to a medical handheld device, and an arrangement for identifying a type of a medical handheld device connected with the power unit according to the invention.

BACKGROUND OF THE INVENTION

Medical handheld devices with electrical consumers are typically operated with accumulators that are being used as voltage sources. This facilitates operating them independently from a power grid and for example close to a patient. The voltage sources are typically components of so-called power units together with additional components, wherein the power units are also designated as power packs. Power units of this type have different configurations and functions.

BRIEF SUMMARY OF THE INVENTION

It is an object of the present invention to provide a power unit with additional functions. Furthermore, a respective medical handheld device and a respective arrangement shall be provided.

The object of the invention is achieved through A power unit including a voltage source; a motor; an arrangement which identifies at least one feature of a handheld medical device and emits a signal caused by the at least one identified feature or based on the at least one identified feature; and/or a circuit board, wherein the power unit is receivable in or at the handheld medical device in a disengageable manner. It is furthermore achieved through a medical handheld device including at least one power unit and/or at least one feature which is identifiable through the identification arrangement. The invention also relates to an arrangement for identifying a handheld medical device that is connected with the power unit, wherein the arrangement identifies at least one feature of the handheld medical device and puts out a signal caused by the identified feature or based on the identified feature, wherein the arrangement is usable with the power unit and/or with the handheld medical device.

The power unit according to the invention includes a particularly one component or multi component arrangement for identification through which at least one feature of the medical handheld device is identified. Based on the result of the identification, the arrangement puts out a signal which reflects or considers the presence or the configuration of the feature or which is based on the feature.

The power unit according to the invention furthermore includes at least one voltage source, a motor and/or a control circuit board. The power unit is suitable and/or provided and/or configured to be removably received in or at a medical handheld device.

The invention furthermore relates to a medical handheld device with at least one power unit according to the invention and/or with at least one feature which is provided and/or embodied to be identified through the arrangement for identifying the power connection.

Furthermore, the invention relates to an arrangement for identifying which is configured to identify at least one feature of the medical handheld device and configured to put out a signal caused by the identified feature or based on the identified feature wherein the signal is put out to a component of the power unit.

Advantageous embodiments of the present invention are respectively objects of the dependent claims and embodiments.

Embodiments according to the invention can have one or plural of the features recited infra.

In subsequent embodiments, the language "can be" or "can have", etc., is synonymous with "is advantageously" or "has advantageously", etc., and intended to describe particular embodiments of the invention.

In all subsequent embodiments when an arrangement, a device or other physical means is recited that is configured to perform a method step, it is understood that the present invention also includes the respective means or discloses it herewith, wherein the means is configured, required, prepared and/or provided to perform the respective step.

The power unit is disengageable or removable again in some embodiments according to the invention (disengageable or removable are equivalent configurations that are both within the scope of the invention), thus the power unit is not permanently fixated in or at the handheld device according to the invention.

In some embodiments according to the invention, a receiving section of the medical handheld device for receiving the power unit is closed with a cover, for example a lid or a similar closure. The cover can be supported in a closed position through bolts and/or snap locking closures.

A disengageable embodiment includes for example snap hooks made from plastic material which snap lock in or at the handheld device when the power unit is connected with or in the handheld device. For disengaging the power unit, the elastic snap hooks are deformed and the power unit can be separated from the handheld device.

Identifying a feature in some embodiments according to the invention means reading out, detecting, processing, registering, measuring and/or valuating the feature and combinations of the steps recited supra.

A feature of the handheld device which is identified through the arrangement for identifying and/or reading out at least one feature of the handheld device represents or encodes in some embodiments according to the invention a detectable feature of the handheld device or an inherent function associated with the handheld device. Among these are for example the provided function of clockwise rotation of a drill in a handheld drill (embodiment of a medical handheld device). This function can be encoded through a feature that is configured accordingly and stored together with a meaning of its encoding. Through the arrangement the function can be encoded based on the feature.

In particular embodiments according to the invention, encoding is not performed through electronic storage elements for data. Electronic storage elements for data can be erasable memories or memory elements with integrated circuits which are read out for example through electronic readers. Another embodiment of a feature of the handheld device is applying an adapter to the medical handheld device. An applied drill chuck adapter that is encoded by the feature and represented by the feature in a recognizable manner can also be identified by the arrangement. The same applies for example for an applied adapter for an oscillating saw, for a collet adapter or similar. They can all be encoded and stored at the handheld device so that they are readable by the arrangement through accordingly configured features.

In some embodiments according to the invention, the handheld device and/or the power unit is provided and/or configured and/or prepared in particular for surgery applications.

In particular embodiments according to the invention, the handheld device and/or the power unit is not provided and/or configured and/or prepared for dental applications.

Furthermore a feature of the medical handheld device can be a particular type, e.g. a manufacturer specific device type or a particular model series or it can encode for this purpose. Based on the feature in these cases, for example the handheld device as such can be identified, for example as a handheld drill, a handheld saw or similar.

A feature can be read out touch-free according to the invention or it can be read out through physical contacts. Combinations thereof are within the scope of the invention.

Thus, in particular embodiments according to the invention the feature is a pressure that is generated through the handheld device at a particular location wherein the pressure is identified by the arrangement, in this case measured or sensed. The pressure of the pressure signal can be a mechanically, hydraulically, pneumatically or otherwise generated pressure.

In some embodiments according to the invention a feature that is based on a mechanical pressure is determined through a key switch as an embodiment for an identification device. A key switch in turn can put out an electrical signal as a consequence when the key switch is mechanically activated or pressed (keying pressure).

In particular embodiments according to the invention the mechanical pressure is applied to a key switch through a pin or another geometrically formed component or through a mechanical section. Put differently, the mechanical activation, the keying pressure recited supra is generated through a pin or another geometrically formed component. Thus, the presence of the pin and also the generation of the keying pressure through the pin can be a feature of the handheld device that is identifiable through the arrangement of the power unit.

In particular embodiments according to the invention the mechanical formed component is a bolt or a pin or a plurality thereof.

The mechanical formed component can be made from metal, plastic material, fiber reinforced materials or from other materials or combinations thereof.

A feature that is readable touch-free in some embodiments according to the invention is a barcode, a color marking, a feature that can be read out through LEDs functioning as transmitter and for example photo-diodes functioning as receiver, through ultrasound, laser methods, infrared, RFID (for example with 100 kHz to 6 GHz) or through electromagnetic waves and similar or combinations thereof.

In particular embodiments according to the invention, features that can be read out touch-free are read out through passive and/or permanent storage elements. This can exclude erasable non-permanent data storage elements. Erasable nonpermanent data storage elements can be rewritable, so that data can be stored and erased repeatedly.

Also these and additional not further recited markings can be provided in order to be identified by the identification arrangement. The arrangement can be configured and arrange accordingly.

In some embodiments according to the invention, the feature of the handheld device that is identifiable through the arrangement of the power unit is only identifiable when the handheld device is starting to be used or after the handheld device has started to be used or when the handheld device is provided with voltage or also with mechanical power. For example, a plunger whose presence can be a feature of the handheld device can only be identifiable for the arrangement when an actuation element of the handheld device is actuated like for example a hand push button that is pressed by the user for actuating a motor.

In some embodiments according to the invention, the feature is arranged at the handheld device in a disengageable or modifiable manner. This provides an advantageous option to subsequently change or extend the suitability, the application, etc. of the handheld device in as far as this is required for supporting the power unit, for example through activating or deactivating functions.

In particular embodiments according to the invention, the feature of the handheld device that is identifiable by the arrangement of the power unit is only provided when manually actuating a switch, when actuating a suitable mechanism (transmission, lever, plunger, etc.) or through a medium (for example through applying a hydraulic pressure).

In some embodiments according to the invention the feature of the handheld device that is identifiable through the arrangement of the power unit is already identified through the arrangement of the power unit before starting to use the handheld device. This can be provided for example during or due to connecting the power unit with the handheld device or in a receiving section thereof.

In particular embodiments according to the invention, a feature includes one or plural embodiments or sub-features or feature combinations. A feature can thus encode a plurality of functions or similar.

Subsequently, without being limited thereto, examples for the features and their embodiments are described in a purely exemplary manner. The embodiments of the subsequent features which are considered independent features in particular embodiments according to the invention are recited in parentheses. For example the feature "direction of rotation" with the embodiments "right- and left-rotation", "only right rotation", "only left rotation": rotation direction (right and left rotation, only right rotation, only left rotation), torque (higher than a predetermined torque value, lower than a predetermined torque value), speed (lower than a predetermined speed), drill chuck adapter (inserted, not inserted), saw adapter (inserted, not inserted, oscillating, oscillating below a predetermined frequency, oscillation stroke below a predetermined stroke value), collet adapter (inserted, not inserted, collet force limited to a predetermined value), unit type (permissible, non-permissible, identification number provided, identification number not provided).

Features of the handheld device as described supra can be identifiable or encoded through geometric sections (e.g. pins, edges, plungers, etc.). However, also other configurations can be used for identifying particular features or their embodiments. In an exemplary manner reference is made to the barcode recited supra and the color markings.

The signal which is put out by the arrangement of the power unit represents the presence or non-presence or the configuration or degree (for example high, low) of the feature or considers these or is based thereon.

The signal put out by the arrangement can reflect the identified feature as such, its presence / non-presence and/or its embodiment, for example in a signal form or a signal strength. Thus, the signal is put out in some embodiments according to the invention in consideration of the feature, thus in consideration of its embodiment, its configuration and/or its presence or its non-presence.

In some embodiments of the invention, the signal is put out through a signal receiver within the power unit. The signal, for example an electrical signal, can be forwarded within the power unit and/or changed, in particular exclusively within the power unit. Alternatively thereto, the signal is put out from the power unit changed or unchanged.

In particular embodiments according to the invention, the signal can be triggered through actuating a switch or plural switches.

In some embodiments according to the invention, the signal is a composite signal.

In some embodiments according to the invention, the signal is a permanent signal. A permanent signal is transmitted as long as the respective feature is provided for the identification arrangement.

In other embodiments according to the invention, the signal is a non-recurring signal or a signal that only persists for a limited time period.

In some embodiments according to the invention, the signals put out based on the identified feature are processed through electrical circuits or flow in another manner into a circuit or influence the circuit.

Key switches, for example, are actuated through key pressure and can thus close or open electrical contacts. The closed or opened contacts can activate, control or regulate various functions through the circuits.

In some embodiments according to the invention, the motor is controlled and/or regulated through electrical circuits. For example, particular motor speed ranges can be activated or deactivated, the direction of rotation of the motor can be determined (e.g. only right rotation or only left rotation), particular motor torque ranges can be activated or deactivated, etc. The signal can influence the motor control or -regulation in this manner through the circuit.

In particular embodiments according to the invention the signal is an optical signal. An optical signal can be for example a light beam, a laser beam, an infrared beam, an ultraviolet beam or another beam. An optical signal can be emitted by a light emitter, e.g. by a light diode, an infrared light source, etc. For receivers for the optical signals electronic components can be used, e.g. photo diodes, photo transistors, photo thyristors etc.

In some embodiments according to the invention optocouplers are being used to provide a galvanic separation between the signal transmitter and the signal receiver. Thus, a direct electronic separation between transmitter and receiver can be provided.

The signal can be an optical signal, an electrical signal, a magnetic signal, a capacitive signal, a resistance or another signal.

Each effect or consequence of the signal can be a direct or an indirect consequence. A direct consequence is for example interrupting a power supply or switching a switch. An indirect consequence is provided for example when the signal is not effective by itself or not effective unless previously modified or only jointly effective with other variables.

Electrical signals can be generated through voltage sources and/or magnetic fields (induction principle). Electrical signals can be generated or modified through a series of components and physical effects as they are known to a person skilled in the art. For example, the signals can be generated through elastic deformation of a solid element (piezo electric effect) or through electronic components (resistors, capacitors, coils, integrated circuits, semiconductor diodes, etc.).

In some embodiments according to the invention, the medical handheld device (also abbreviated as handheld device) is a surgical handheld device, for example configured as a handheld drill or handheld saw, for example configured as an oscillating handheld saw, for example for orthopedic applications or emergency surgery. The handheld device according to the invention can also be provided for other medical applications like for example dental technology, oral surgery, neurosurgery, arthroscopy, etc.

In particular embodiments according to the invention, the handheld device includes at least one bar code (or plural bar codes), a color marking, a geometric section, (wherein the section is also designated as a mechanical formed component herein) or combinations thereof. These are identified in some embodiments according to the invention by the identification arrangement for identifying at least one feature of the medical handheld device.

The identifying in these embodiments can include for example to check and to communicate the result of the check through generating and putting out a respective signal, whether a particular or plural particular geometric sections (this also applies for bar codes, color markings etc.) are provided at the handheld device. Thus, for example the presence of a pin in a housing opening of the power unit can lead to activating a switch within the power unit and thus to putting out a signal. The feature, thus a provided pin can stand for a "right turning function of a drill in a handheld drill provided as a medical device". In this case the pin is a marker or an identifier which acts as a feature and encodes a function and which is used for identifying the feature.

The pin can be a section of the medical device which establishes a connection and/or a contact with the power unit which is disengageably received in the medical device. The features, thus the provided pin, however, can also directly encode that the particular handheld device which includes the pin is a handheld drill.

The handheld device can certainly include two or plural geometrically identically or differently configured pins (this certainly in turn also applies for bar codes or bar code lines or color markings, etc.) through which a respective independent feature is encoded. Alternatively, the plurality of pins can also jointly encode or identify a single feature. Thus, the presence of each pin in a position at the handheld device that is provided for this purpose can encode a feature, thus also the presence of a particular combination of pins in the respectively provided positions at the handheld device can encode a common feature. For example, three pins can be varied in three provided positions so that eight different features can be identified through the following combinations: three pins provided in all three positions, no pins provided, one pin provided in the first position, one pin provide in the second position, one pin provided in the third position, a respective pin provided in the first position and in the second position, a respective pin provided in the first position and in the third position, and a respective pin provided in the second and in the third positions.

Four pins can already encode 16 features by themselves or one feature can be encoded by 16 different features that exclude one another, wherein the features can be read out through the identification device, For five pins, the number already expands to 32 features or feature combinations, etc. Mathematically, this can be computed by the second power of the number of pins.

In some embodiments of the invention, a feature, for example the recited pin, besides its presence or non-presence, can also encode a function through its particular configuration. For example a provided pin can be configured short or long, thin or thick, etc. This increases the number of possible functions, suitabilities, device types, etc. that are differentiateable through the encoding without generating additional complexity.

In particular embodiments according to the invention, the power unit is configured to be used with at least two different embodiments (also designated as types of medical handheld devices), in particular optionally sequentially or alternatively. The feature for identifying a medical handheld device can facilitate a determination with which of the at least two different embodiments of medical handheld devices the power unit is connected in the moment when the feature is identified or with which handheld devices the power unit is being connected.

In some embodiments according to the invention the at least two different configurations or types of provided handheld devices are provided for use in independent applications, thus for example for drilling on the one hand side and sawing on the other hand side. Simultaneously, however, these are all provided in the embodiments according to the invention to be used together with the same power unit and to be supplied with energy by the power unit.

The handheld devices provided in at least two different embodiments can be provided for use in different functions or applications. They can differ for example through various configurations, different designs, and similar.

In particular embodiments according to the invention the power unit includes an electrical circuit and/or a motor. The electrical circuit can include one or plural electronic components. The electrical circuit can be a section of a circuit board on which additional circuits and/or electronic components are arranged.

In particular embodiments according to the invention the power unit includes an arrangement for adapting the power unit to the medical handheld device and/or for associating the power unit with the medical handheld device based on the signal or the feature. In these embodiments, as stated supra, a feature of the medical device is identified and a signal is put out which is based on the previously identified feature or which reflects this feature. The signal can cause or be used for activating different functions in the power unit or to deactivate them (for example motor parameters) for example through electronic components on a circuit board in the power unit. Thus, these functions control or regulate the medical handheld device. Put differently, the identified features are used for adapting the power unit, its power, its support of the handheld device, etc. to the medical handheld device. A functional context between the power unit and the medical handheld device is established or associated through the identified feature and through the signal put out according to the identified feature.

In particular embodiments according to the invention, the power unit includes an arrangement for providing at least one actuation device of the handheld device with one or plural functions or for generating or canceling at least one provision of the actuation device of the medical handheld device with a predetermined function. This is provided respectively directly or indirectly based on the signal or in consideration of the signal.

In particular embodiments according to the invention the actuation device of the medical handheld device is a trigger (or button, actuation switch) which controls or activates the motor of the power unit. Through a provision of the actuation arrangement, for example the adjustability of the rotation direction of the motor or the switchability of its running direction can be determined through a particular actuation arrangement through the user. Thus, the user is enabled for example to change the rotation direction of a drilling tool of the handheld device through actuating a particular actuation device. Alternatively it is possible to enable the user to predetermine a torque range or to limit the maximum achievable speed of the motor instead of the running direction when actuating the same actuation device.

In some embodiments according to the invention, the provision of at least one such actuation device is directly or indirectly based on the signal which was put out due to an identified feature by the device in the power unit.

In a particular embodiment according to the invention, the power unit includes an arrangement for activating and/or deactivating at least one function in or at the medical handheld device based on the signal, thus it can be defined for example through this device that a switch for switching between left hand rotation and right hand rotation of the employed tool is rendered non functional. This can for example be performed when the power unit detects based on the identified feature of the actually used handheld device that this is no handheld drilling device but for example an oscillating hand saw.

In other embodiments according to the invention, the power unit includes a device for controlling and/or regulating the motor and/or the voltage source and/or a circuit board, in particular a motor circuit board of the power unit based on the signal.

In particular embodiments according to the invention, the power unit includes a device which is provided and/or configured to check based on the signal based on already provided information whether the power unit is suitable or configured at all to be used with the handheld device. Provided information can be particular device types or particular device functions and the usability of the power unit for this purpose. The power unit can be suitable for example for some device types or device functions or can be certified for use herewith or for this purpose but not for others. Based on the signal which is generated by the identification arrangement, the question of usability of the power unit for the particular handheld device can be checked and answered automatically. Depending on how the result of this check comes out, the use of a particular device type or a particular function can be activated or deactivated. The already provided information can result from tables, memories and similar and can be stored for example on a circuit board e.g. in an EPROM (abbreviation for: erasable programmable read only memory).

The voltage source of the power unit in some embodiments according to the invention includes one or plural rechargeable accumulators for electrical energy. The accumulator or the accumulators include one or plural cells.

Plural accumulators can be connected in order to increase voltage and/or capacity or they can also be connected separately so that another accumulator is used after a first accumulator has been emptied, for example in order to recharge the first accumulator.

In some embodiments according to the invention, the charging condition of the accumulator is indicated, e.g. through LEDs (light emitting diodes). The LEDs can be arranged in a housing of the power unit or of the handheld device so that the charging condition is determinable from an outside.

The charging condition of the accumulators, however, can also be displayed in other ways, for example through an acoustic or optical alarm when undercutting a predetermined charging condition, through telemetric interrogation of sensors which indicate the charging condition or other methods.

Accumulators can be provided on an electrochemical basis (so-called galvanic cells) or they can be based on other physical/chemical principles.

In particular embodiments according to the invention the medical handheld device does not include any power users, no voltage source, no motor, no circuit board and/or no electronic control device unless these are provided in or at the power unit or form a part thereof.

This can advantageously facilitate to sterilize the handheld device according to the invention without the power unit, wherein no power consumer, no voltage source, no motor, no circuit board and/or no electronic control device has to be subjected to a possibly detrimental sterilization process which is required for the handheld device (e.g. steam sterilization, hot air sterilization, radiation sterilization (for example gamma ray sterilization), plasma sterilization or another sterilization method).

In particular embodiments according to the invention, the medical handheld device is a hand drill, a hand saw or an oscillating hand saw.

The term "handheld device" as used in the instant application stands for a device that does not include a power unit. Where this is evidently the case for a person skilled in the art, the term is also used for a handheld device with an inserted or connected power unit.

In some embodiments according to the invention the device according to the invention is a control-, regulation- and/or identification-device.

Embodiments according to the invention can include one or plural of the advantages recited supra or infra.

One advantage of the embodiment according to the invention is avoiding using the power unit in medical devices which are not suitable for being used with this power unit. This advantageously prevents an erroneous use which can have severe consequences in a medical application.

Another advantage is that the medical device can be advantageously simplified for handling by operators through the control options based on the signals based on the identified features. The controlled switching on and switching off or adaptation of particular functions advantageously simplifies the operation of the medical device. Since this step can be automatically performed according to the invention, time is being saved in an advantageous manner.

It is another advantage of the present invention that the detection between power unit and handheld device can be configured simple, robust and maintenance free.

It is another advantage that a detection of the handheld device type through the power unit is possible without support by personnel or users through the embodiments according to the invention. Human error where it is being forgotten to perform a required adaptation of the power unit to the particular handheld device is advantageously excluded.

BRIEF DESCRIPTION OF THE DRAWINGS

Subsequently, the present invention is described in an exemplary manner with reference to schematic drawing figures in which identical reference numerals designate like or similar components, wherein.

DETAILED DESCRIPTION OF THE INVENTION

Figure 1:
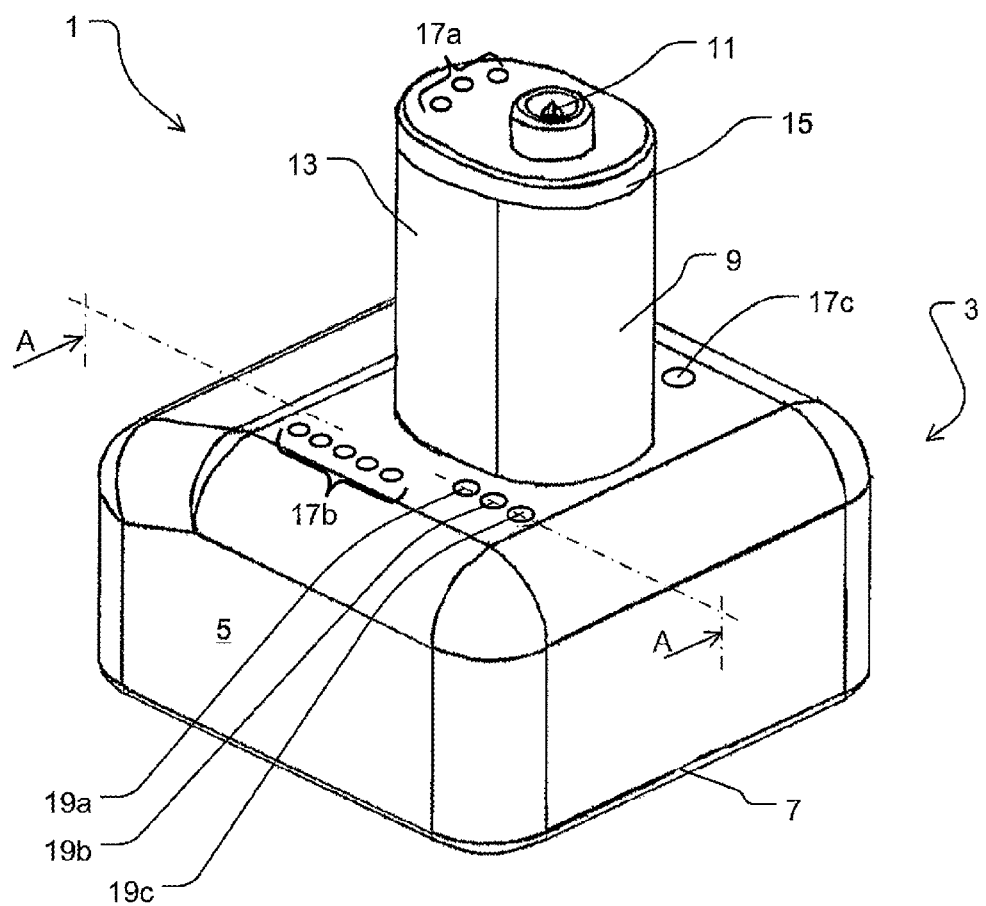
FIG. 1 illustrates a power unit in an exemplary embodiment according to the invention in a perspective view.

FIG. 1 illustrates the power unit 1 according to the invention in an exemplary embodiment in a perspective view at a slant angle from above.

Figure 2:
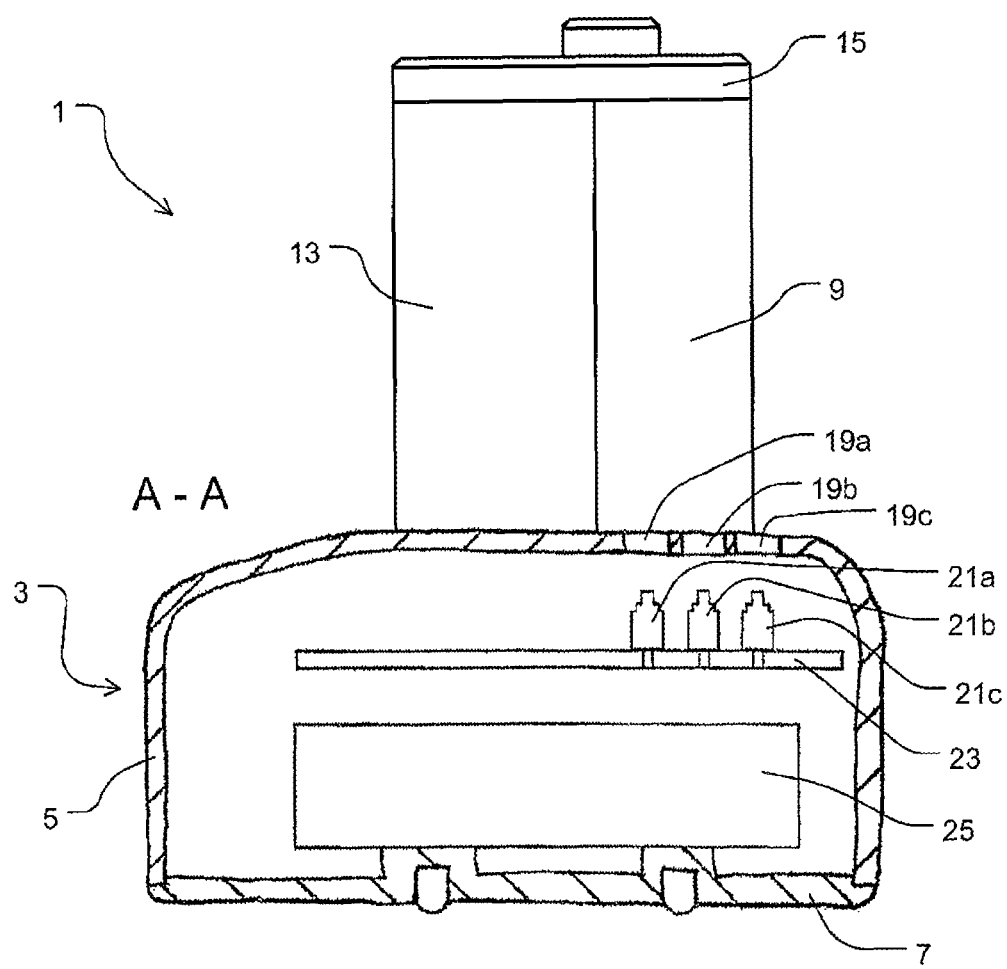
FIG. 2 illustrates the power unit according to the invention according to FIG. 1 in a sectional view along the dash-dotted line A-A of FIG. 1.

The power unit 1 includes a base section 3 with a housing 5 and a lower cover 7 (configured as a power unit cover which can be opened and closed). The base section 3 includes hidden below its housing 5 among other elements a rechargeable voltage source configured as an accumulator with one or plural cells. Furthermore, one or plural control and regulation components (circuit boards, etc.), mechanical components and devices configured as switches 21a, 21b and 21c (not visible in FIG. 1, c.f. FIG. 2) are arranged in the base section 3.

Above the base section 3 of the power unit 1, a motor 9 is arranged with an output shaft or clutch 11 which is attached at the motor 9 or the motor shaft. An additional shaft or a transmission can be connected for example through this coupling 11. The motor 9 is supplied by the voltage source of the base section 3. Another voltage source, e.g. through network supply is not provided in the associated handheld device. The voltage source arranged in the base section 3 can supply additional electrical components of the power unit 1 in addition to the motor 9.

Laterally at the motor 9, an additional component 13 is arranged in which for example an additional control- or regulation component for the motor or for the voltage source is arranged.

The motor 9 and the component 13 include a joint upper cover 15. Pass through openings 17a are arranged in the cover 15 which lead through the cover 15. The pass through openings can be used as an access, for example for mechanical plungers or pins to the electrical components in the power unit 1, for example in order to use contacts of circuit boards, for example for a power- or voltage tapping for electrical consumers outside of the power unit 1.

Housing pass through openings 17b and 17c can also be used as an access to electrical components within the power unit 1. For example, a mechanically controllable turn regulator can adjust or control a turn potentiometer which is arranged in the power unit 1.

Furthermore, three pass-through openings 19a, 19b, 19c are arranged on the top side of the base section. Through these pass-through openings 19a, 19b, 19c which reach through the housing 5 into an interior of the power unit 1, pins 33a, 33b, 33c can be run that are not illustrated in FIG. 1 for the handheld device 27 according to the invention that is also not illustrated in FIG. 1. Thus, the pins 33a, 33b, 33c code for the actually provided handheld device 27. The pins 33a, 33b, and 33c thus correspond to a feature which is processed by the non-illustrated identification device. Reference is thus made to the subsequent description of FIGS. 3 through 7.

The sectional plane along the dash-dotted line A-A is illustrated in FIG. 2.

FIG. 2 illustrates the power unit 1 according to the invention looking at the sectional plane along the dash-dotted line A-A illustrated in FIG. 1. Components arranged behind this line like the motor 9, the component 13 and the cover 15 are not sectioned due to the routing of the sectional line.

The device according to the invention for identifying features of a medical handheld device 27 (cf. FIG. 3 through 7) is illustrated in this exemplary embodiment as a switch 21a (or in the same configuration as 21b, 21c) or at least includes these switches. The switch 21a is embodied herein as a micro switch or a key switch for triggering an electrical signal. The switch 21a in this embodiment is directly attached to a circuit board 23. The electrical signal is transmitted to the circuit board 23 and can be processed further therein and/or can be forwarded from there, for example to control and regulation components on or outside of the circuit board 23.

The power unit 1 further includes a voltage source 25 (illustrated herein in a schematically simplified manner).

Other components that are included by the power unit 1 like e.g. additional circuit boards, control and regulation components, mechanical components, etc. are not illustrated in FIG. 2 for simplification purposes.

Figure 3:
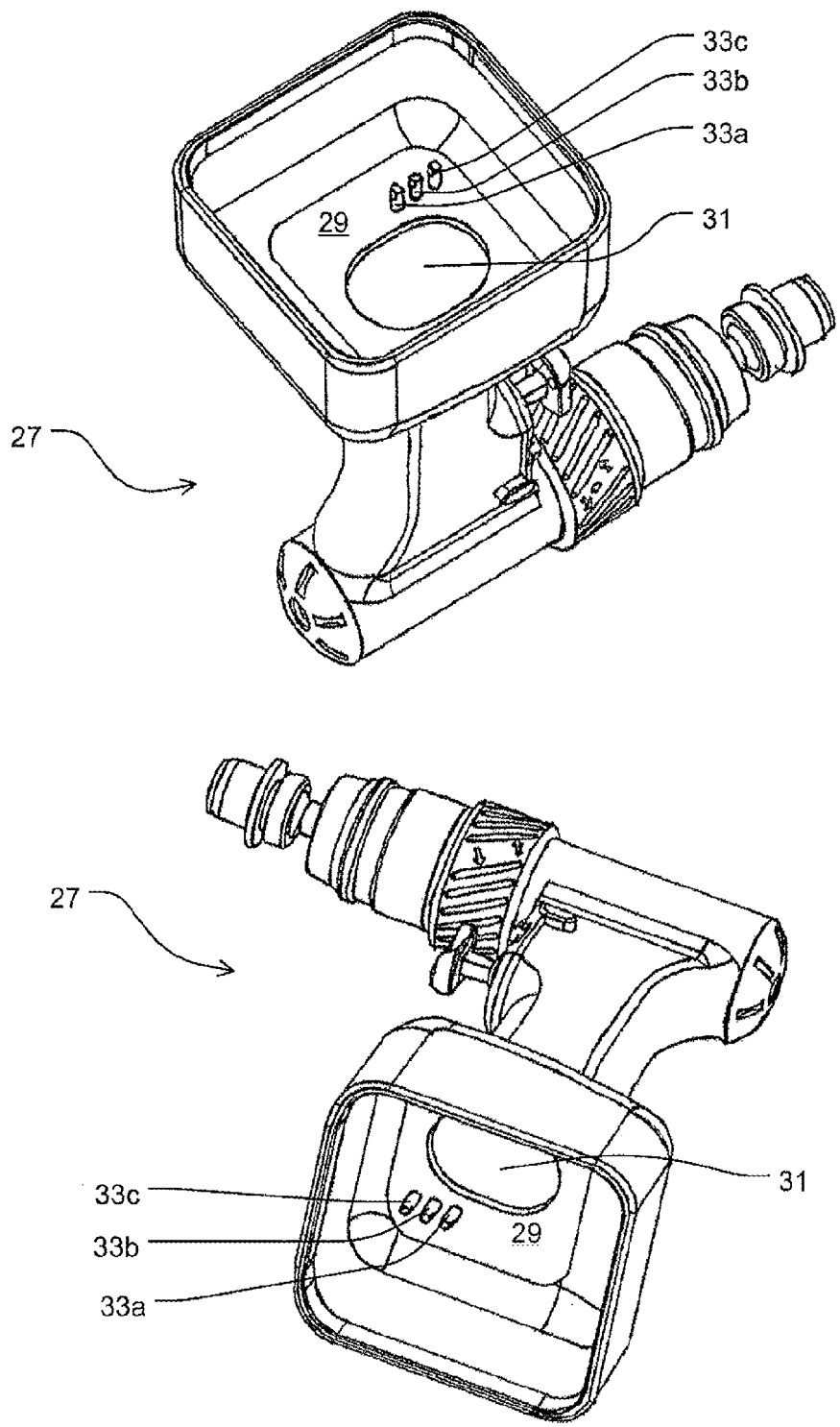
FIG. 3 illustrates a first embodiment according to the invention of a medical handheld device in two perspective views respectively without power unit.

FIG. 3 illustrates a medical handheld device 27 according to the invention in two perspective views at a slant angle from below, illustrated herein respectively without power unit 1 and lower cover 7.

The medical handheld device 27 is illustrated in this embodiment in a purely exemplary manner as a surgical hand drill.

A receiving section 29 for the power unit 1 includes an opening 31 for the motor 9 and the component 13. Furthermore, three pins 33a, 33b and 33c are illustrated which are in this case disengageably threaded or inserted into the receiving section 29, whereas they are not disengageable in other embodiments according to the invention and can thus not be manipulated intentionally or unintentionally and they are connected with the receiving section 29 or form a portion thereof. The pins 33a, 33b, 33c are used as a feature based on which the handheld device is detected. Their function is described in more detail in FIGS. 4 through 7.

Figure 4:
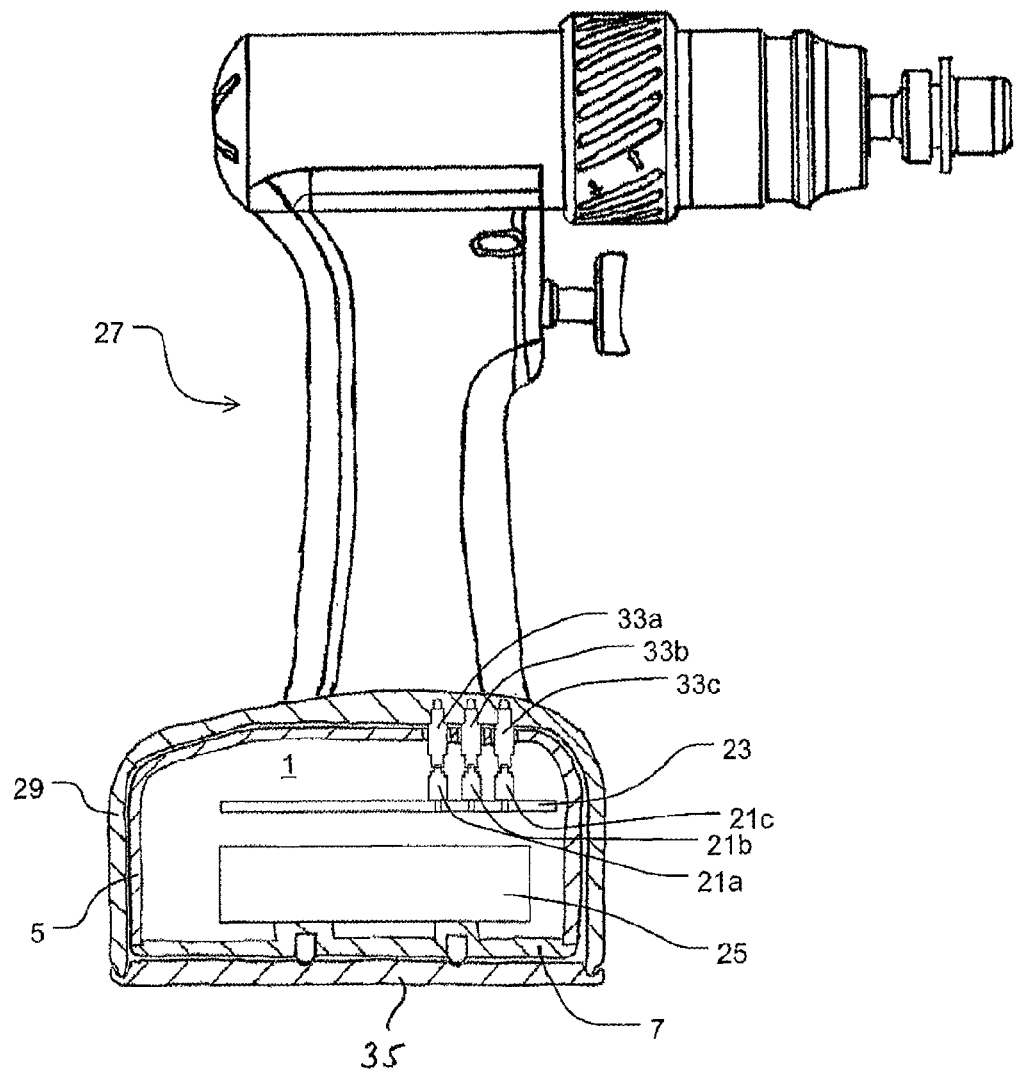
FIG. 4 illustrates the medical handheld device according to the invention according to FIG. 3 in a partial sectional view from a side with the power unit sectioned along the dash-dotted line A-A in FIG. 1.

FIG. 4 illustrates the medical handheld device 27 of FIG. 3 in a side view. The power unit 1 and the lower cover 7 are illustrated in a sectional view along the dash-dotted line A-A of FIG. 1.

The pins 33a, 33b, 33c that are threaded or inserted into the receiving section 29 are run through the housing pass-through openings 19a, 19b, 19c (cf. FIG. 1) when the power unit 1 is inserted into the receiving section 29. After the power unit 1 is completely inserted into the receiving section 29 and a handheld device cover 35 closes the receiving section 29, the pins 33a, 33b and 33c press onto the respective switches 21a, 21b and 21c which respectively triggers an electrical signal when an electrical voltage is applied to these switches 21a, 21b, and 21c, or establishes an electrical connection. The switches 21a, 21b, 21c forward these signals to the circuit board 23 or through the circuit board 23 and can trigger various functions that are provided in the power unit 1. Functions of this type can also be programmed in certain components, for example in the circuit board 23.

Examples for functions triggered based on the actuation of the switches 21a, 21b, 21c include parameters for operating the motor 9 (for example activating/deactivating a high speed or a low speed) or activating/deactivating a right turning function or a left turning function, for example directly through the motor control or through a signal to a transmission in the medical handheld device 27 outside of the power unit and much more.

Figure 5:
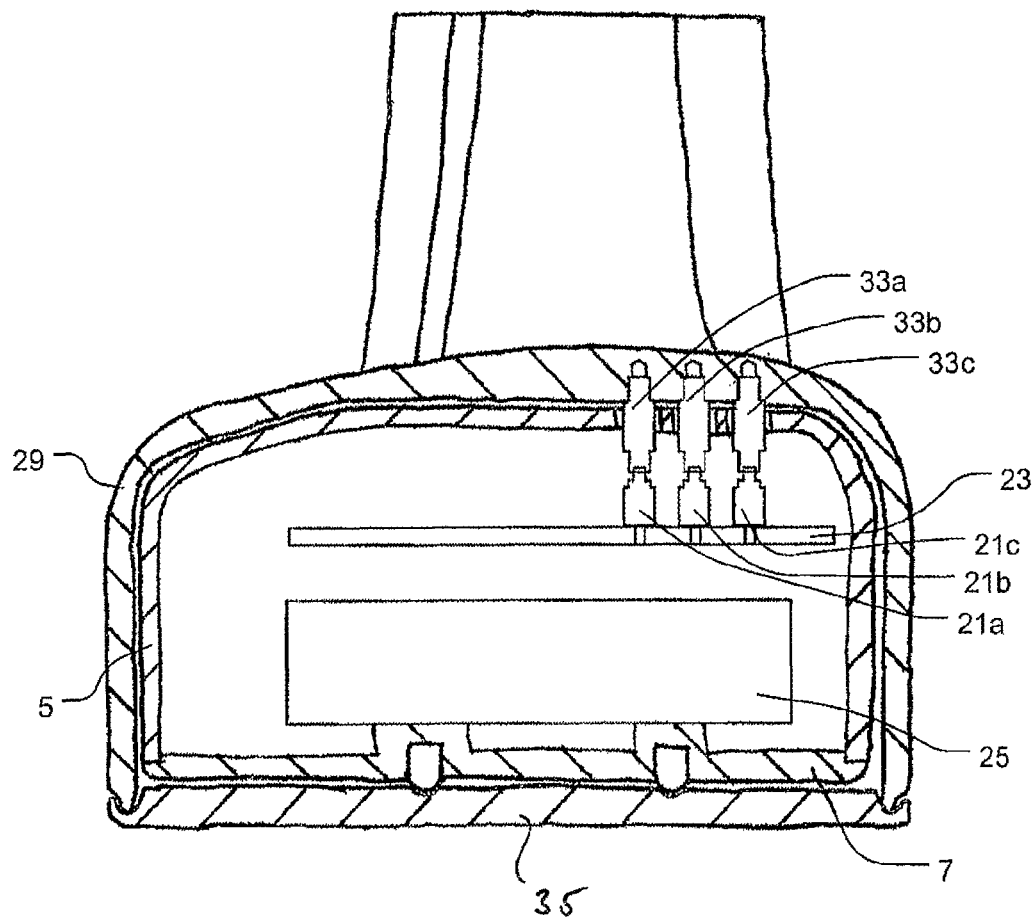
FIG. 5 illustrates a detail of FIG. 4.

FIG. 5 illustrates a detail of FIG. 4.

Figure 6:
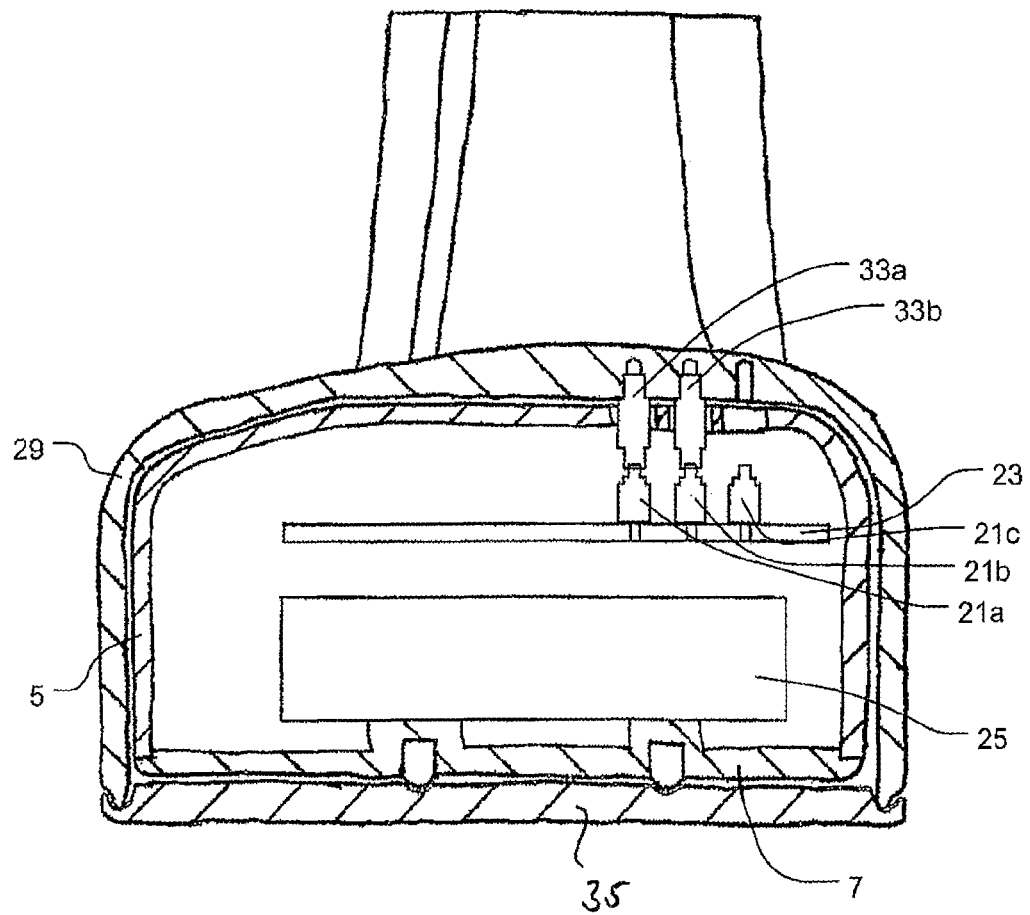
FIG. 6 illustrates a handheld device according to the invention in a second embodiment in a depiction analog to FIG. 5.

FIG. 6 illustrates a handheld device according to the invention in a second embodiment in an illustration that is analogous to FIG. 5

Figure 7:
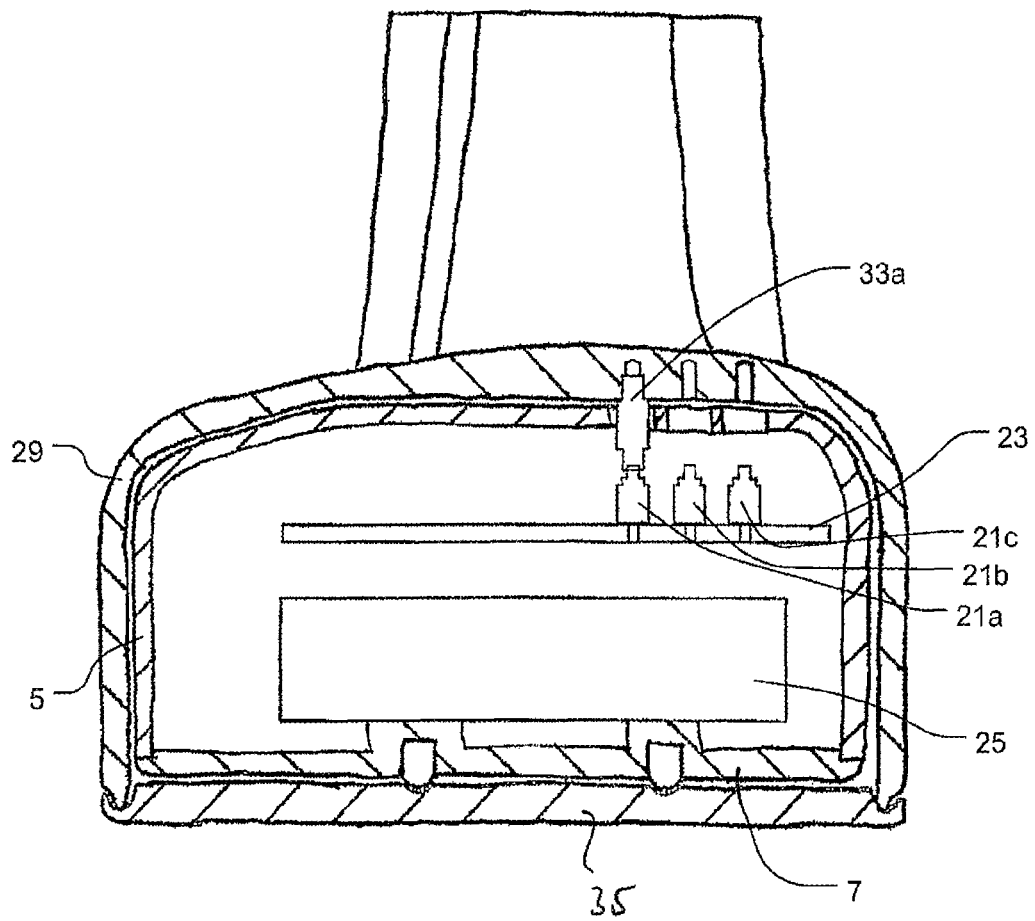
FIG. 7 illustrates a handheld device according to the invention in a third embodiment in a depiction analogous to FIG. 5 and FIG. 6.

FIG. 7 illustrates a handheld device according to the invention in a third embodiment in an illustration analogous to FIG. 5 and FIG. 6.

Thus FIGS. 5 through 7 illustrate the lower portion of the medical handheld device 27 as a sectional view with different respective pin arrangements 33a, 33b, 33c. FIG. 5 includes all three pins 33a, 33b, 33c, FIG. 6 includes two pins 33a, 33b, and FIG. 7 only includes pin 33a.

In FIG. 5, all three switches 21a, 21b and 21c are activated. In FIG. 6 two switches 21a, 21b are activated and in FIG. 7 only the switch 21a is activated.

The pin arrangements in FIGS. 5 through 7 are only selected in an exemplary manner, any other arrangement, for example with the pin combinations 33a and 33c, 33b and 33c, only 33b or only 33c are also feasible. The switches 21a, 21b, and 21c are activated accordingly when a respective pin is associated with a respective switch or the handheld device 27 includes a respective pin.

Any arrangement or combination of pins 33a, 33b, and 33c can trigger different functions. Depending on the switch activation, different signals are put out to the circuit board 23. The put out signals or signal combinations can control or regulate particular motor functions, activate LEDs (not illustrated in the figures) or can control or regulate other functions in the power unit 1 or in the medical handheld device 27.

REFERENCE NUMERALS AND DESIGNATIONS 1 power unit
3 base section
5 housing
7 lower cover
9 motor
11 coupling
13 component
15 upper cover
17a, b, c housing pass through openings
19a, b, c housing pass through openings
21a, b, c switches, arrangements
23 printed circuit board; electric circuit
25 voltage source; accumulator
27 medical handheld device
29 receiving section
31 opening
33a, b, c pins; mechanical formed components
35 handheld device cover

What is claimed is:
1. A power unit, comprising:
a voltage source;
a motor;

an arrangement which identifies at least one feature of a handheld medical device and emits an emitted signal reflecting the at least one identified feature based on an engagement of the power unit with the handheld medical device; and a circuit board, wherein the power unit is receivable in or at the handheld medical device in a disengageable manner, and wherein the at least one feature is a pressure generated through the handheld medical device at a particular location and the pressure is identified by the arrangement.

2. The power unit according to claim 1, wherein the emitted signal is an optical signal or a capacitive signal.

3. The power unit according to claim 1, wherein the emitted signal is an electrical signal or a magnetic signal.

4. The power unit according to claim 1,
wherein the power unit is usable with at least two or more handheld medical devices, and
wherein the at least one feature differentiates the at least two or more different embodiments of handheld medical devices.

5. The power unit according to claim 1, wherein the power unit includes an electrical circuit and a motor.

6. The power unit according to claim 1, wherein the power unit includes a device for at least one of adapting the power unit to the handheld medical device based on the emitted signal or the at least one feature and of associating the power unit with the handheld medical device based on the emitted signal or the at least one feature.

7. The power unit according to claim 1, further comprising an arrangement for providing at least one actuation device of the medical handheld device with a predetermined function based on the emitted signal.

8. The power unit according to claim 1, further comprising a device for activating or deactivating at least one function in or at the handheld medical device based on the emitted signal.

9. The power unit according to claim 1, further comprising an arrangement for controlling or regulating the motor of the power unit based on the emitted signal.

10. The power unit according to claim 1, further comprising an arrangement for checking the emitted signal based on provided information whether the power unit is usable with the handheld medical device.

11. The power unit according to claim 1, Wherein the at least one feature is, represents or encodes a detectable feature of the handheld device or an inherent function associated with the handheld device.

12. The power unit according to claim 1, wherein the arrangement identifies the at least one feature of the handheld medical device through a key switch.

13. The power unit according to claim 12, wherein the pressure is applied to the key switch through a mechanical section or a mechanical component.

14. A medical handheld device, comprising at least one power unit comprising:
a voltage source;
a motor;
an arrangement which identifies at least one feature of a handheld medical device and emits a signal reflecting the at least one identified feature based on an engagement of the power unit with the handheld medical device; and a circuit board, wherein the power unit is receivable in or at the handheld medical device in a disengageable manner, wherein the at least one feature is a pressure generated through the handheld medical device at a particular location, or at least one feature which is identifiable through an arrangement configured to identify at least one feature of a handheld medical device and to emit a signal reflecting or considering the presence or the configuration of caused by the at least one identified feature or which is based on the at least one identified feature, and wherein the pressure is identified by the arrangement.

15. The medical handheld device according to claim 14, wherein the handheld medical device includes at least one mechanical formed component or at least one geometrical section for identifying the at least one feature.

16. The medical handheld device according to claim 14, wherein the handheld medical device includes at least one shaft or one transmission which are connectable with the motor of the power unit.

17. The handheld medical device according to claim 14, wherein the handheld medical device is sterilizable without the power unit.

18. The handheld medical device according to claim 14, wherein the handheld medical device is a handheld drill or a handheld saw or an oscillating handheld saw or a handheld saber saw or a handheld sagittal saw.

19. The handheld medical device according to claim 14, wherein the handheld medical device further comprises a switch or an actuating mechanism for identifying the at least one feature.

20. The handheld medical device according to claim 14, wherein the handheld medical device further comprises a key-switch for identifying the at least one feature.

21. The handheld medical device according to claim 14, wherein the medical handheld device does not include any power users, voltage source, motor, circuit board nor electronic control device unless these are only provided in or at the power unit.

22. The handheld medical device according to claim 14, wherein the power unit includes a device which is provided or configured to check based on the emitted signal whether the power unit is suitable or configured to be used with the handheld device.

23. A power unit with additional functions, comprising:
a voltage source;
a motor; and
an arrangement which identifies at least one feature of a handheld medical device and emits an emitted signal reflecting the at least one identified feature based on an engagement of the power unit with the handheld medical device; and wherein the power unit is receivable in or at the handheld medical device in a disengageable manner, wherein the power unit is usable with at least two or more handheld medical devices, wherein the at least one feature differentiates the at least two or more handheld medical devices, wherein the at least one feature causes the power unit to be adapted to the handheld medical device, and wherein the motor is controlled or regulated based on the emitted signal.

* * * * *